United States Patent [19]

Hoffmann et al.

[11] Patent Number: 4,807,291
[45] Date of Patent: Feb. 21, 1989

[54] CIRCUIT FOR A FLASH STROBOSCOPE FOR EXAMINING VOCAL CHORD FUNCTIONS

[75] Inventors: Reiner Hoffmann, Illingen; Peter Jaggy, Oetisheim, both of Fed. Rep. of Germany

[73] Assignee: Richard Wolf GmbH, Fed. Rep. of Germany

[21] Appl. No.: 917,692

[22] Filed: Oct. 10, 1986

[30] Foreign Application Priority Data

Oct. 17, 1985 [DE] Fed. Rep. of Germany ....... 3536972

[51] Int. Cl.$^4$ .......................... A61B 1/26; G10L 9/04
[52] U.S. Cl. ...................................... 381/49; 128/773; 315/241 S
[58] Field of Search ...................... 381/48, 49; 128/10, 128/11, 773; 354/62; 356/23-26; 315/241 S

[56] References Cited

U.S. PATENT DOCUMENTS

| | | | |
|---|---|---|---|
| 2,244,687 | 6/1941 | Goldsmith et al. | 352/49 |
| 2,244,688 | 6/1941 | Goldsmith et al. | 352/49 |
| 2,343,971 | 3/1944 | Goldsmith | 358/41 |
| 2,867,209 | 1/1959 | Foures et al. | 128/6 |
| 3,244,167 | 4/1966 | Ferris et al. | 128/6 |
| 3,599,630 | 8/1971 | Sato et al. | 128/6 |
| 4,175,545 | 11/1979 | Termanini | 128/666 |
| 4,219,104 | 8/1980 | Oshiro et al. | 187/9 R |
| 4,222,394 | 9/1980 | Nagashima et al. | 381/49 X |
| 4,232,685 | 11/1980 | Nagashma et al. | 128/773 |
| 4,273,949 | 6/1981 | Tuda et al. | 381/48 |
| 4,349,014 | 9/1982 | Takamatsu | 128/6 |
| 4,384,775 | 5/1983 | Hosoda | 354/62 |
| 4,416,524 | 11/1983 | Takayama | 354/416 |
| 4,423,436 | 12/1983 | Kimura | 358/98 |
| 4,616,636 | 10/1986 | Nagashima et al. | 356/23 X |

Primary Examiner—Patrick R. Salce
Assistant Examiner—Emanuel Todd Voeltz

[57] ABSTRACT

A circuit for a flash stroboscope for examining vocal chord functions has a number of band-pass filters connected in parallel which have different cut-off frequencies. The acoustic signal generated by the vocal chords is fed to the inputs of these filters as an electrical signal after conversion in an electro-acoustic transducer. The output signal or fundamental wave signal allowed to pass by filter with a fundamental frequency of interest for the examination is supplied to a lamp circuit, which activates a flash lamp by trigger pulses generated from the fundamental wave. The band-pass filters are scanned automatically and successively to determine the presence of an output signal having the fundamental frequency of interest. The scanning operation is stopped upon detection of an output signal of this frequency at one of the filter outputs, so that the output of this filter can be connectd to the lamp circuit. The scanning operation is repeated cyclically so that the circuit can always be updated to the existing condition in the event of possible changes of the fundamental wave frequency.

16 Claims, 2 Drawing Sheets

FIG. 1

CIRCUIT FOR A FLASH STROBOSCOPE FOR EXAMINING VOCAL CHORD FUNCTIONS

BACKGROUND OF THE INVENTION

1. Field of the Invention

The present invention relates to flash stroboscopes for use in examining vocal chord functions, and in particular to a frequency identification circuit for such a stroboscope.

2. Related Application

The present application is related to the co-pending application entitled "Video Endoscope" filed Mar. 4, 1987 and assigned Ser. No. 021,809, for which Felix Ams, Reiner Hoffman and Peter Jaggy are named as inventors.

3. Description of the Prior Art

Stroboscopes are utilized in the medical field for diagnosing vocal chord defects most advantageously in combination with a laryngoscope. This permits the physician to observe the larynx illuminated with a standard light and the vocal chords in their natural appearance and behaviour, and also provides the possibility, by a frequency synchronized illumination of the vocal chords, to observe the vibrating vocal chords as a frozen image.

The comparatively short light flashes illuminate the vocal chords consistently at the same point of a cyclic displacement stage so that a still image is generated. A slowed down movement of the vocal chords may also be deliberately observed in the manner of a suspension effect, by means of a phase shift, by varying the flash instant in the course to consecutive oscillations.

In order to accomplish the above observation, it is necessary to know the fundamental wave or fundamental frequency at which the vocal chords vibrate, because the operating frequency of the stroboscope must be tuned to this frequency. Instruments are known with which one can filter out the fundamental wave signal from an acoustic signal, for example, an acoustic signal generated by a vowel sung or spoken by a patient. Such circuits undertake an appropriate switching among various filters. Thereafter, pulses are generated from this fundamental wave with which it is possible to control the flash lamp circuit. When the light flashes thus generated illuminate the vocal chords by means of a laryngoscope, the observer sees a still picture, provided that the fundamental frequency does not change.

If a change occurs in the fundamental frequency, however, the physician must attempt to determine the new frequency range in which the fundamental wave signal now lies, so that the apparatus can be reset to the frequency range in question by appropriate switching of the filters. Using conventional instruments, the physician must simply make a judgment on a subjective basis, so that erroneous settings of the apparatus will be likely to occur, since the accuracy of the settings depends in large part on the acuteness of the physician's hearing. The interruptions caused in the examination of the patient by the switching operations are also troublesome and time consuming. In conventional units it has also been noted that frequently the follower or overrun filters used in such units are comparatively slow, and the filters lock on to harmonics which are not of interest, rather than onto the fundamental wave as desired.

SUMMARY OF THE INVENTION

It is a object of the present invention to provide a circuit for a flash stroboscope which permits an automatic, rapid, precise and reliable determination of the fundamentai frequency or fundamental wave or an incoming acoustic signal, despite the presence of harmonics and which automatically adapts to spontaneous variations of the fundamental wave frequency with minimum reaction times.

The above object is achieved in accordance with the principles of the present invention in a circuit, wherein the filters are automatically successively scanned to determine the presence of an output signal from one of the filters having the fundamental frequency of interest. Upon such an output signal being detected at one to the filter outputs, the scanning operation is stopped and the output or the filter in question is connected to the lamp circuit for controlling triggering of the lamp, and the scanning operation is cyclically repeated. The filter which permitted the fundamental wave to pass is maintained switched through to the lamp circuit notwithstanding the continuing scanning operation, until a different filter permits the signal having the actual fundamental wave to pass upon the occurrence of a change in the fundamental frequency. At this point, the output of the other filter is connected to the lamp circuit in place of the original filter.

With a circuit of this type, the signal carrying the fundamental wave needed for evaluation is automatically available even given intervening changes of the incoming fundamental wave frequency. The signal, is,,moreover available at its actual signal strength. The physician does not have to intervene for the purpose of searching for the new fundamental frequency, and the circuit operates very precisely and rapidly with appropriate organizations of the filters and other components.

The fundamental wave signal which is permitted to pass in each case by a filter is converted into a d.c. signal by a rectifier circuit, so that the outputs or the rectifier circuit can be scanned by a multiplexer. The multiplexer is connected to a comparator which, via a control logic, initiates incrementation of an address counter at the repetition rate of the scanning operation. The address counter counts the number of filter outputs scanned since the beginning of the scanning operation and transmits this number to a second multiplexer via an address memory. The second multiplexer switches to the filter output corresponding to the count in the memory and supplies the fundamental wave signal permitted to pass by the filter to the lamp circuit. The comparator may change to a different logic switching state upon detecting a fundamental wave signal at one of the filter outputs scanned, and there upon emits a stop command to the address counter via the control logic system. The counter reading is stored in the address memory and the second multiplexer is placed at a setting corresponding to this counter reading.

The output signals of the filters are converted into d.c. signals by a peak value rectifier system, so that the first multiplexer can scan the momentary state of charge of the capacitors in the rectifier circuits. The charge must be neutralized before the beginning of each new scanning operation after updating the counter reading and after setting the second muitiplexer. This is accomplished by a discharge signal from the control logic.

DESCRIPTION OF THE PREFERRED EMBODIMENTS

Figure 1:
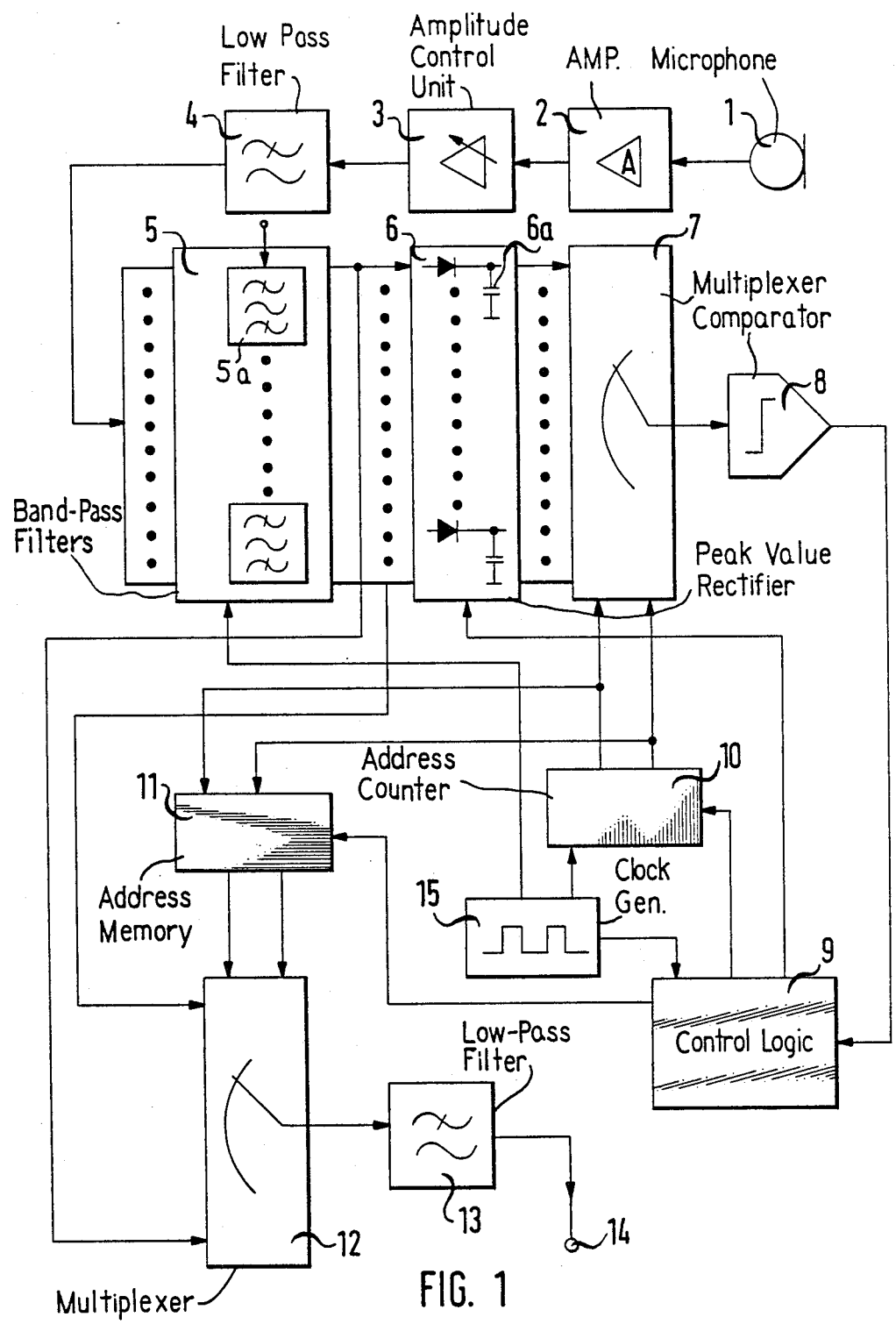
FIG. 1 is a schematic block circuit diagram of a circuit for a flash stroboscope for examining vocal chord functions constructed in accordance with the principles or the present invention.

As shown in FIG. 1, an acoustic signal generated by a patient is received by a microphone 1 and is amplified by an amplifier 2. The signal is then supplied to an amplitude control unit 3 which may be, for example, an operational amplifier, which sets the output signal to a constant value without distortion. The signal is then supplied to a low-pass filter 4 which has a cut-off frequency tuned to the highest frequency of the total measuring range of interest such as, for example, 1500 Hz. This simplifies the layout and functions of the following circuit elements because these elements need not process signals at higher frequency levels.

The low-pass filter 4 should not generate any linear distortions in the pass range of the signal which, in addition to the fundamental wave, contains harmonics. For this purpose, Bessel filters are particularly appropriate, these having a constant group delay in the pass range.

The output of the low-pass filter 4 is connected to inputs of band-pass filters 5 connected in parallel. The band-pass filters 5 may, for example, be switched capacitor filters constructed using MOS technology. These filters can be driven in a known manner by energizing the capacitors thereof with a clock generator 15, having an operating frequency substantially above the cut-off frequency of the filters.

As shown by testing, an adequate measuring range and selection in connection with the fundamental waves which are to be filtered are obtained for examining vocal chord functions with a total of fifteen band-pass filters 5 having a relative overall band width of five octaves. The lower frequency of the first filter is 50 Hz and the upper cut-off frequency to the last tiiter is 1500 Hz.

Use may be made ot so-called triple-third octave filters to produce a combination of this type. These are three single filters which have a band width of one third of an octave and which overlap each other at their 3 dB points so as to form in combination a pass-band having an amplitude of an octave. For this purpose, the cut-off frequencies of the band-pass filters are fixed at intervals in steps of a third. A first filter $5a$ in the plurality of filters 5 may have an input as schematically indicated by the arrow for selecting the lower cut-off frequency thereof in order to adapt to different applications.

By connecting five such filters in parallel, a band-pass system is obtained having fifteen individual filters with a relative overall amplitude of five octaves and a measuring range from 50 to 1500 Hz. The clock feed to the filters is comparatively uncomplicated because, starting with the filter having the highest cut-off frequency, the clock signal for the other filters can be obtained by binary division.

The respective outputs of the band-pass filters 5 are supplied to respective peak value rectifier circuits 6, so that the output signals of the filters are respectively rectified. The filter outputs after rectification are scanned cyclically by a first multiplexer 7, which scans the charge levels or the capacitors $6a$ belonging to the rectifier circuits 6 from bottom to top.

The output of the multiplexer 7 is supplied to a comparator 8 which, upon detecting an output signal meaning that a specific charge level in one capacitor $6a$ for a particular band-pass signal has exceeded a predetermined level, switches from a first logic state to a second logic state, such as from logic "0" to "1". Upon this occurrence, control logic 9 receives a command from the comparator 8 to stop an address counter 10 connected to the multiplexer 7. If fifteen band-pass filters 5 are provided in accordance with the above example, and for example the eighth band-pass filter allows the fundamental wave signal to pass and appear at the output, the comparator 8 will switch states at the eighth setting of the multiplexer 7, and the address counter 10 will be stopped by the control logic 9. The address counter 10 is incremented at the repetition rate of the scanning operation until stopped by the control logic 9.

The reading of the address counter 10 is then stored in an address memory 11, which places a second multiplexer 12 at a switching position corresponding to the existing counter reading (the eighth position in the above example) so that the multiplexer 12 switches the eighth band-pass filter 5 to the output 14. The output of the multiplexer 12 may be supplied to the output 14 through another low pass filter 13. The output 14 is supplied to the lamp circuit shown in FIG. 2, described below.

After storing the count of the address counter 10 and setting the second multiplexer 12, the address counter 10 is reset and the capacitor $6a$ are discharged by respective signals t rom the control logic 9. This permits another scanning operation by the first multiplexer 7 to be automatically started after a specific measuring period.

The filter 5 which permitted the fundamental wave to pass will remain switched through to the lamp circuit notwithstanding these further scanning operations, until a change in the fundamental frequency causes another signal including the actual fundamental wave to pass. Upon this occurrence, the output of this other filter is connected to the lamp circuit via the second multiplexer 12. The address memory 10, and thus the connection of the signal-carrying filter 5 to the output 14 via the multiplexer 12 are maintained at the existing condition in connection with the fundamental frequency. As the low pass filter 4 described above, the low pass filter 13 is tuned to the highest fundamental wave frequency occurring in the measuring range or interest, i.e., 1500 Hz in the example discussed above. Aside from this, the low pass filter 13 should eliminate the clock frequency contained in the output signal of the band-pass filters controlled by the clock generator 15 as well as intermodulation frequencies, so that no disturbances occur in the lamp circuit.

Figure 2:
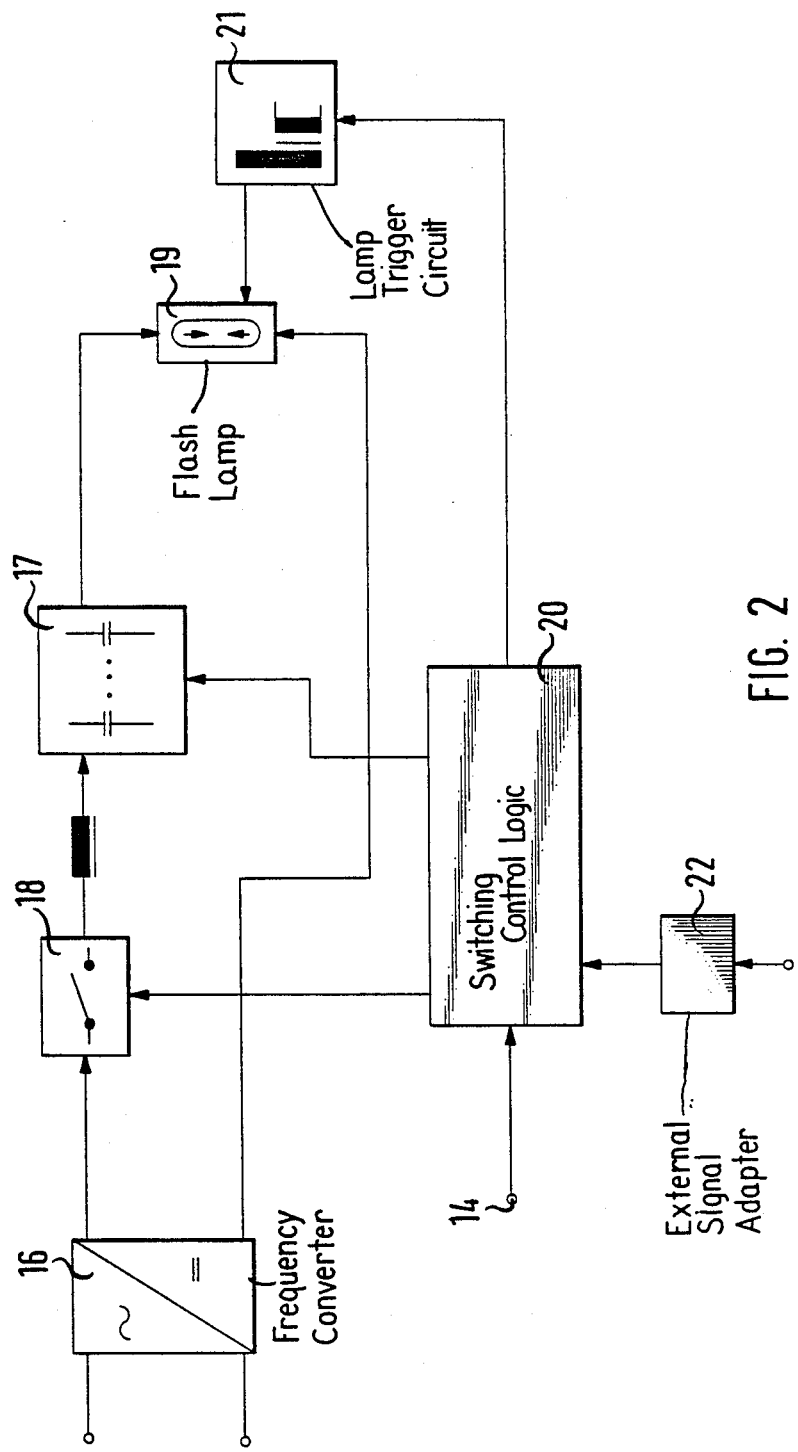
FIG. 2 is a schematic block diagram of a known lamp circuit of the type operated by the output of the circuit shown in FIG. 1.

The lamp circuit shown in FIG. 2 is a conventional stroboscopic circuit and need only be briefly described. The circuit includes a frequency converter 16, which charges a number of capacitors 17 automatically as a function of power frequency upon the closing or charging contacts 18. The capacitors 17 are connected in parallel with a flash lamp 19, and can be discharged via the flash lamp 19 under the control of switching control logic 20. The flash lamp 19 is momentarily placed in the discharge circuit branch by a trigger circuit 21, which is energized upon the occurrence of the fundamental wave frequency or the acoustic signal generated by the vocal chords by means or an internal frequency generator which may be integrated in the switching control logic 20. Alternatively, such a signal may be externally applied via an external signal adaptor 22.

If the fundamental wave frequency and the flash frequency coincide, a still image of the vocal chords under examination is obtained. The phase setting and frequency may, however, also be varied by the switching control logic 20 so that a suspended image is obtained, i.e., the vocal chords may be optically observed in slow-motion. A shift of the phase setting is also possible, for observing a particular point of the vocal chords on an apparently stationary image. The switching control logic 20 may also perform other functions, such as generating (and it necessary converting) control pulses developed ±rom the fundamental wave or supplied via the external signal adaptor 22.

Although modifications and changes may be suggested by those skilled in the art it is the intention of the inventors to embody within the patent warranted hereon all changes and modifications as reasonably and properly come within the scope of their contribution to the art.

We claim as our invention:

1. A circuit for operating a flash lamp in a lamp drive circuit in synchronization with the fundamental frequency of an incoming acoustic signal of variable fundamental frequency comprising:
   transducer means for converting said acoustic signal into an electric signal;
   a plurality of band-pass filters connected in parallel having respectively different pass-bands to which said electric signal is supplied;
   means for cyclically scanning the outputs of all of said filters;
   means for detecting the presence of a signal at an output of one of said filters having said fundamental frequency;
   means for stopping said means for scanning upon detection of said signal having said fundamental frequency; and
   means for connecting the output of said one of said filters to said lamp drive circuit for use as a control signal for said lamp drive circuit.

2. A circuit as claimed in claim 1 further comprising:
   means for re-activating said means for scanning until said fundamental frequency of said incoming signal varies and said means for detecting detects a signal at an output of a different one of said filters having said fundamental frequency, whereupon said means for connecting connects the output of said different one of said filters to said lamp drive circuit.

3. A circuit as claimed in claim 1, further comprising:
   means connected between said outputs or said band-pass filters and said means for scanning for rectifying said outputs of said band-pass filters.

4. A circuit as claimed in claim 3, wherein said means for scanning the outputs of all of said filters is a multiplexer.

5. A circuit as claimed in claim 1, wherein said means for detecting is a comparator connected to the output of said multiplexer, said comparator changing state when the rectified output of one of said filters exceeds a predetermined level.

6. A circuit as claimed in claim 5, further comprising an address counter enabled by said comparator and which stops counting upon said change of state of said comparator for identifying the position of said multiplexer corresponding to the filter at which said output signal having said fundamentai frequency is present.

7. A circuit as claimed in claim 6, further comprising:
   a memory for storing said count or said address counter upon stopping thereof by said comparator; and
   an additional multiplexer having an output connected to said lamp drive circuit, the position of said an additional multiplexer being set by the contents of said memory for connecting the output of said one of said filters to said lamp drive circuit.

8. A circuit as claimed in claim 1, further comprising:
   means connected to the outputs of said plurality of band-pass filters for rectifying the respective outputs thereof, said means for rectifying having a like plurality or capacitors respectively charged by the outputs of said filters;
   said means for scanning the outputs of all of said filters sampling the respective charge levels of said capacitors; and
   means for discharging said capacitors simultaneously with stopping said means for scanning.

9. A circuit as claimed in claim 8, wherein said means for scanning is a multiplexer.

10. A circuit as claimed in claim 1, further comprising:
    a first low pass filter connected between said transducer means and the inputs of said plurality of band-pass filters; and
    a second low pass filter connected between said means for connecting and said lamp drive circuit, said first and second low pass filters having the same limit frequency, said limit frequency coinciding with an upper limit frequency or a band-pass filter in said plurality of filters for a highest fundamental frequency of said plurality.

11. A circuit as claimed in claim 1, wherein each of said band-pass filters in said plurality of band-pass filters has a respective limiting frequency set at maximum intervals of octave steps.

12. A circuit as claimed in claim 10, wherein said plurality of band-pass filters in combination have an overall band-width of at least one octave, and wherein a cut-off frequency of a first filter or said plurality filters is selectable.

13. A circuit for operating a flash lamp in a lamp drive circuit in synchronization with the fundamental frequency of an incoming acoustic signal of variable fundamental frequency comprising:
    transducer means for converting said acoustic signal into an electrical signal;
    a plurality of band-pass filters connected in parallel having respectively different pass-bands to which said electric signal is supplied;
    a first multiplexer for scanning the respective outputs of said plurality of filters;
    a comparator connected to the output of said first multiplexer, said comparator changing state when a signal having said fundamental frequency appears at the output of one of said filters;
    an address counter connected to said first multiplexer and to an output or said comparator, the count of said address counter being incremented with each change in position of said first multiplexer as said first multiplexer scans said filter outputs, and said address counter stopping upon said change of state of said comparator at a count corresponding to said filter with said output signal having said fundamental frequency;

an address memory connected to said address counter for storing the count of said address counter occurring at said change of state of said comparator; and a second multiplexer having a plurality or inputs respectively connected to said outputs of said band-pass filters and an output connected to said lamp drive circuit, said second multiplexer being set by said address memory to a position corresponding to said count or said address counter at which said comparator changed state for connecting the output of said filter with said signal having said fundamental frequency to said lamp drive circuit for use as a control signal for said lamp drive circuit.

14. A circuit as claimed in claim 13, further comprising:

means connected between said outputs of said band-pass filters and said inputs of said multiplexer for rectifying the respective outputs of said filters, said means for rectifying including a plurality of capacitors respectively connected to said outputs of said filters and being respectively charged thereby, said first multiplexer scanning the respective charge levels of said capacitors.

15. A circuit as claimed in claim 12, further comprising:

a low pass filter connected between said transducer means and the inputs of said plurality of band-pass filters, said low pass filter having a limit frequency coinciding with the upper limit frequency of one of said band-pass filters for a highest fundamental frequency.

16. A circuit as claimed in claim 15, further comprising:

an additional low pass filter connected between the output of said second multiplexer and said lamp drive circuit, said additional low pass filter having a limit frequency which is the same as the limit frequency of said low pass filter.

* * * * *